United States Patent [19]

Lauer et al.

[11] Patent Number: 5,224,863
[45] Date of Patent: Jul. 6, 1993

[54] FILLING ASSEMBLY FOR DOLL WITH LIQUID RESERVOIR

[75] Inventors: Daniel J. Lauer, St. Louis; Howard J. Hlina, Maryland Heights, both of Mo.

[73] Assignee: Lauer Toys Incorporated, St. Louis, Mo.

[21] Appl. No.: 729,812

[22] Filed: Jul. 17, 1991

Related U.S. Application Data

[63] Continuation-in-part of Ser. No. 616,333, Nov. 21, 1990, which is a continuation-in-part of Ser. No. 571,754, Aug. 22, 1990, abandoned.

[51] Int. Cl.⁵ .................................. G09B 23/28
[52] U.S. Cl. .................... 434/267; 446/224; 446/220; 446/267
[58] Field of Search ............... 141/348, 349, 350, 331; 220/307, 353, 202; 446/224, 220, 267, 304; 434/267

[56] References Cited

U.S. PATENT DOCUMENTS

| | | | |
|---|---|---|---|
| 853,639 | 5/1907 | Hincks . | |
| 1,346,176 | 7/1920 | Chambers . | |
| 1,384,731 | 7/1921 | Richards . | |
| 1,751,773 | 3/1930 | Trosper | 446/304 |
| 1,758,024 | 5/1930 | Blomquist . | |
| 1,761,603 | 6/1930 | Wainwright | 220/307 |
| 2,774,184 | 12/1956 | Hefferan et al. . | |
| 3,174,455 | 3/1965 | Peterson | 446/220 X |
| 3,516,452 | 6/1970 | Scholle | 141/350 |
| 3,664,058 | 5/1972 | Brieske | 446/224 |
| 3,734,149 | 5/1973 | Hansel | 141/350 |
| 3,858,351 | 1/1975 | Porter . | |
| 3,903,942 | 9/1975 | Vest | 141/331 X |
| 3,911,977 | 10/1975 | Berger | 141/348 |
| 4,132,334 | 2/1979 | Danks | 141/348 X |
| 4,185,844 | 1/1980 | Hubbard et al. | 141/348 X |
| 4,209,939 | 7/1989 | Pittala . | |
| 4,242,830 | 1/1981 | Hauser . | |
| 4,492,258 | 1/1985 | Lichtenstein et al. | 141/331 X |
| 4,568,298 | 4/1986 | Acree . | |
| 4,575,351 | 3/1986 | Gonzalez . | |
| 4,678,014 | 7/1987 | Owen et al. | 141/350 X |
| 4,816,000 | 3/1989 | Hsu . | |

FOREIGN PATENT DOCUMENTS

| | | | |
|---|---|---|---|
| 10111 | 1/1929 | Austria . | |
| 675586 | 2/1930 | France | 446/304 |
| 14984 | of 1895 | United Kingdom . | |

Primary Examiner—Richard J. Apley
Assistant Examiner—Karen Ann Jalbert
Attorney, Agent, or Firm—Armstrong, Teasdale, Schlafly & Davis

[57] ABSTRACT

An assembly for filling and emptying a liquid reservoir inside a doll, the assembly includes a valve for installation in an opening in the doll body that communicates with the reservoir, and a funnel adapted to cooperate with the valve member to allow liquid to be introduced into or removed from the reservoir. The the valve has a valve body with first and second ends, adapted to be installed in an opening in the doll body with the first end of the valve body extending into the reservoir. A valve passage extends through the valve body between the first and second ends. A valve member at the first end of the valve body is biased to close the valve passage. The funnel has a spout adapted to seat in the valve passage. The end of the spout is adapted to displace the valve member when the spout is seated in the valve passage to allow liquid to pass through the valve passage.

15 Claims, 3 Drawing Sheets

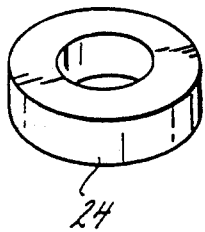
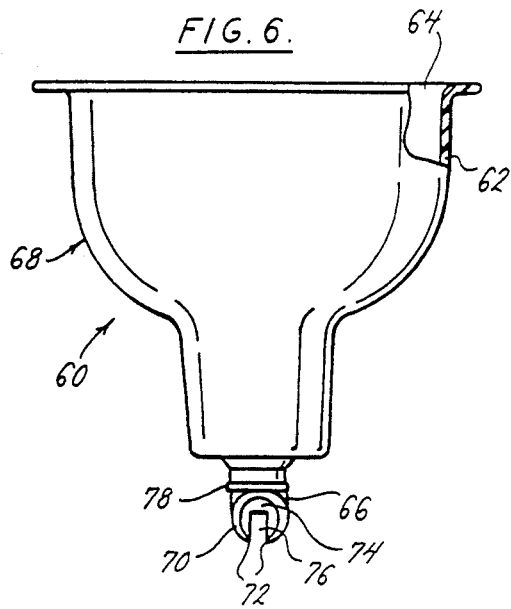
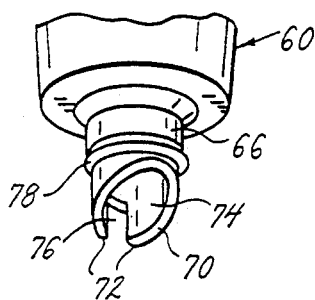
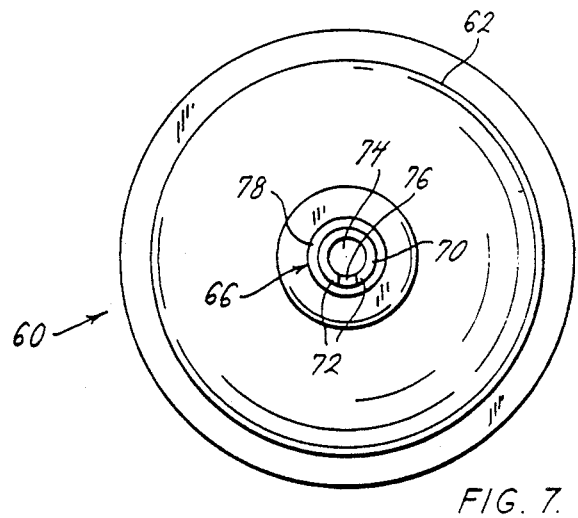
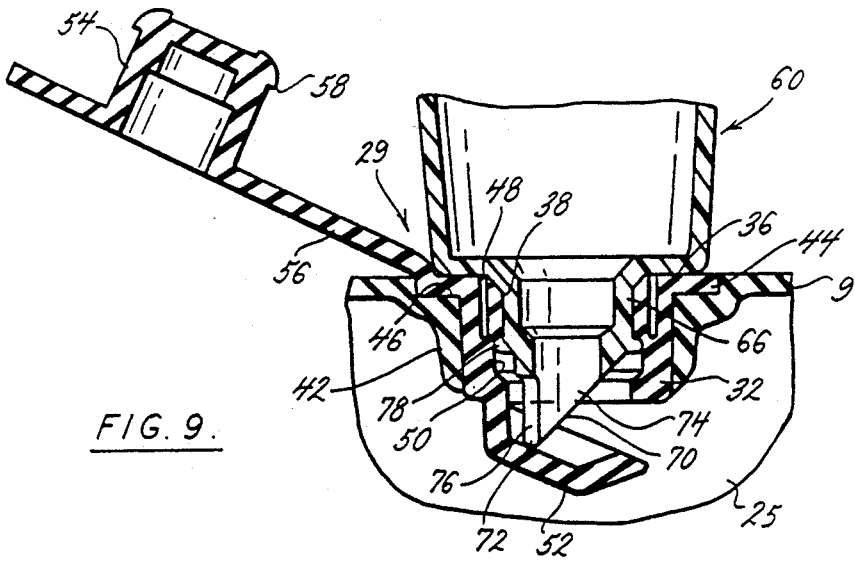

FILLING ASSEMBLY FOR DOLL WITH LIQUID RESERVOIR

CROSS REFERENCE TO RELATED APPLICATIONS

This is a continuation-in-part of pending application Ser. No. 07/616,333 filed Nov. 21, 1990, entitled Infant Doll, which was a continuation-in-part of Ser. No. 07/571,754 filed Aug. 22, 1990, now abandoned.

BACKGROUND OF THE INVENTION

The present invention relates to dolls, and in particular, to newborn infant dolls which provide life-like feel and flexibility. More particularly, the invention relates to infant dolls filled with a liquid medium from the neck down to achieve the described realistic features so that people can be effectively trained in proper infant care and handling, or so that people can simply enjoy playing with a doll with such life-like features.

In the training of those who will be feeding, handling, or clothing newborn infants, as for example, nurses, medical attendants, family members, and particularly children, it is important that they appreciate the newborn infant's weight, size, strength and lack of motor skills, particularly as they relate to control of the infant's head and neck. The newborn infant is very delicate and the slightest mishandling can lead to serious or fatal injury. Feeding or nursing the infant, or bathing, grooming or clothing the child, all require protecting the infant from losing its balance or control of its various limbs, especially its head and neck, and from being subjected to excessive force.

Moreover, young children desire to use dolls that are realistic and which simulate characteristics of live infants. Playing with such dolls is stimulating and enjoyable for young children.

The prior art contains dolls. Some have moveable parts or semicompressable structures, however, the prior art dolls do not provide the life-like feel, mobility, flexibility and structure for teaching proper infant care in handling. Nor do prior art dolls provide such features to enhance the joy and stimulation of young children who play with dolls.

For example, U.S. Pat. No. 4,568,298 to Acree, discloses a doll which has a torso and chest region comprised of a flexible material, such as plastic, which can be filled with liquid. However, the remainder of the body parts are not filled with liquid, and therefore are not compressible and life-like in touch.

More importantly, the arms, legs, and head of the doll are not attached to simulate a realistic resilient feel. The head of the Acree doll is attached to the torso by a rigid filling structure. Thus, the doll's head is not moveable with respect to the doll's torso. Likewise, the arms and legs are comprised of foam filler covered by cloth. This attachment arrangement is extremely flimsy and does not create the resiliency of a real newborn infant's joints. Moreover, such a doll does not provide interactive force among the various body parts.

U.S. Pat. No. 4,242,830 to Hauser discloses a doll having rigid body parts. The doll has a plastic covering over certain portions of its body such that a thin layer of liquid can be contained between the rigid doll structure and the plastic covering. Hauser does not disclose a doll entirely filled with liquid. Additionally, the Hauser doll provides a rigid neck structure that does not teach the user of the doll of the need to support the head of a real infant.

In sum, the prior art does not disclose a doll having a body entirely filled with a liquid medium such that a realistic feel and compressibility of an infant baby is simulated. Moreover, the prior art dolls provide rigid neck structures which do not teach persons using the doll of the proper method for handling and supporting the head of the infant. And the prior art dolls do not disclose a doll that creates appropriate interactive forces among the body parts.

SUMMARY OF THE INVENTION

In accordance with the present invention, a newborn infant doll is provided which is realistic in feel, compressibility, flexibility and structure. The infant doll has a head, neck, arms, torso, and legs. The infant doll has a detachable head which is formed with a substantially stiff but flexible vinyl rubber material which simulates the hard surface of an infant baby's head. The remainder of the infant doll's body, which includes the neck, the torso, the arms, and the legs, is constructed of a less rigid vinyl material which simulates the feel and compressibility of a newborn infant. The housing for the doll is shaped to outline the exterior of an infant, and is proportionate to the shape of an infant, and scaled to be of somewhat smaller size than an infant born during normal gestation.

The housing wall for the neck, the torso, the arms, and the legs creates a reservoir which is capable of being filled with a liquid medium. When a liquid is introduced into the reservoir, the neck, the torso, the arms, and the legs of the infant doll are filled with the liquid, which causes the doll to take on the feel, flexibility, and compressibility characteristics of a real infant baby. Furthermore, since the reservoir is comprised of a contiguous cavity formed in the neck, the torso, the arms, and the legs, hydraulic interactive forces can act against or in response to forces applied to the surface of the body parts, and among the body parts. Thus, when forces are exerted against the surface of these parts, indention of the surface occurs, and a realistic resistive force against such forces results. Further, when a force is exerted upon one of the body parts, a force is transmitted to other body parts, which thereby causes the remaining body parts to move. For example, if one of the legs of the infant doll is wiggled, the arms, the torso, the neck, and the remaining leg will also wiggle. This feature intensifies the concerns that one must have in handling a real infant, by developing appreciation for the fact that what may be considered minor forces to an adult or child have much greater impact and effect on an infant.

The neck of the infant doll is constructed with a flexible housing material. An annular recess is provided in the top of the neck and is capable of receiving a plug that telescopically fits within the recess. The plug strengthens the neck and creates flexibility and resiliency correlative of a real infant's neck. This arrangement teaches users of the doll to provide adequate support for the doll's head.

The infant doll is also provided with a filling assembly which allows liquid to enter into the reservoir. A liquid of a specific temperature may be added so that the temperature of a real infant baby is correlated, including temperatures to simulate the baby having a fever. The water temperature can be controlled to bring the fever down.

The filling assembly comprises a valve, incorporated into the doll. The valve comprises a valve passage communicating with the reservoir, and a valve member inside the reservoir and biased to close the valve passage. The valve member is preferably a flap hingedly mounted over the end of the valve passage. The flap acts as a check valve against spillout, and reduces pressure against the plug in use and while filling the reservoir. A cap or plug may be provided to close the outside of the valve passage and reduce leakage. This design provides ease in operation in filling the reservoir, and a secure locking of the plug to prevent leaks.

The filling assembly also comprises a funnel, having a spout adapted to be inserted into the valve passage. The end of the spout projects into the reservoir when the spout is seated in the valve passage to displace the valve member and allow liquid to be introduced into or removed from the reservoir through the funnel. The funnel not only allows liquid to be introduced into and removed from the reservoir, but it also allows "burping" of air from the reservoir. When the funnel is removed from the opening of the filling assembly, the flap closes automatically, either under the resilience of the hinged mounting, the liquid pressure in the reservoir, or both. The cap can then be inserted into the valve passage to securely close the reservoir.

The foregoing as well as the following set forth objects of the present invention as found in one or more of the claims. It is an object of the present invention to provide a newborn infant doll which can be efficiently manufactured to provide a doll which realistically simulates the feel, compressibility, and flexibility of a real newborn infant.

It is also an object of the present invention to provide an infant doll having a flexible neck structure so that the user of the doll is alerted of the need to support the head of a real infant, and is taught the proper method of handling for the infant's head.

A further object is to provide an infant doll which creates effective transmittal of force among the various doll body parts, and against the doll's skin surface.

And yet another object is to provide an infant doll having its body, from the neck down, completely filled with a liquid medium. Furthermore, an object is to conveniently fill the infant doll with a liquid medium at a selected temperature such that the normal temperature and fever temperatures of an infant doll can be simulated, and to provide a secure seal of the liquid within the doll to prevent leakage.

An additional object is to provide a filling structure for the doll which facilitates introducing a liquid into the doll, minimizes leakage of the liquid from the reservoir, and allows air to be burped from the reservoir.

Moreover, an object of the present invention is to manufacture the infant doll with a flexible material that is sufficiently thick to provide for appropriate durability, and yet not too thick to prevent realistic feel and flexibility. Still another object is to manufacture the doll of a durable flexible material that allows for inexpensive construction of the infant doll.

These and other objects will become apparent in the following description of preferred embodiments.

BRIEF DESCRIPTION OF THE DRAWINGS

FIG. 5 is an elevation view of the cap plug that fits within the doll's neck;

FIG. 6 is a side elevation view of the funnel that is used to fill and empty the reservoir of the doll;

FIG. 7 is a bottom plan view of the funnel;

FIG. 8 is a partial perspective view from below of the spout of the funnel;

FIG. 9 is a cross-sectional view of the filling assembly showing the spout inserted in the valve passage;

Corresponding numerals indicate corresponding parts throughout the drawings.

DETAILED DESCRIPTION OF THE PREFERRED EMBODIMENT

Figure 1:
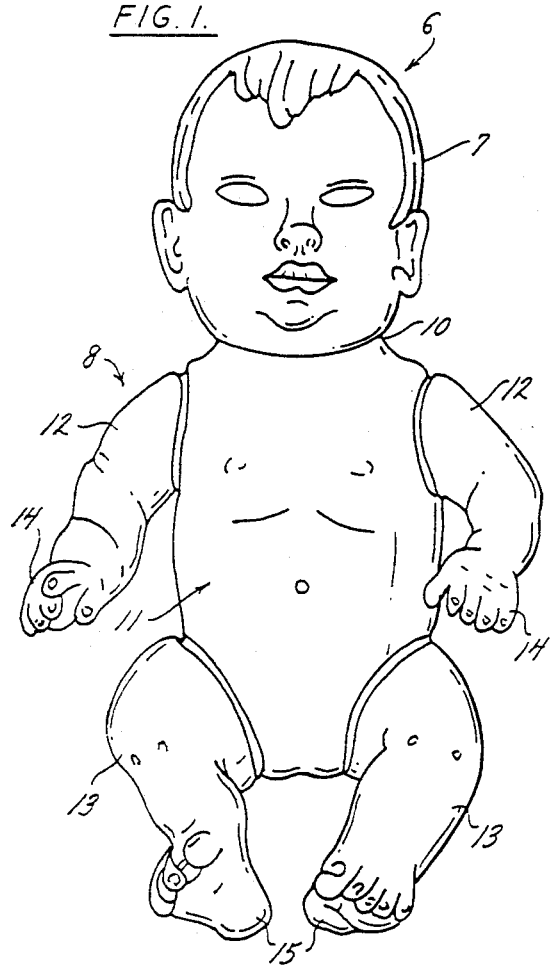
FIG. 1 is a front elevation view of an infant doll incorporating the present invention.
Figure 2:
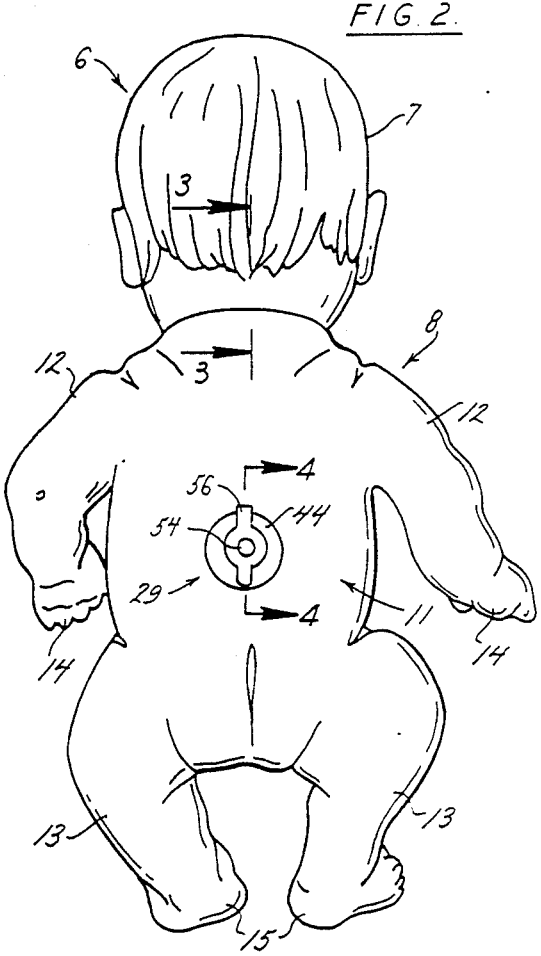
FIG. 2 is a rear elevation view showing the infant doll.

Referring to FIGS. 1 and 2, the infant doll is generally designated 6. It comprises a head section 7, and a separate lower section 8. The lower section 8 comprises a continuous housing wall 9 (shown in FIGS. 3 and 4), which forms a neck 10, a torso 11, arms 12, and legs 13. The arms 12 and legs 13 also comprise hands 14 and feet 15, respectively.

Figure 3:
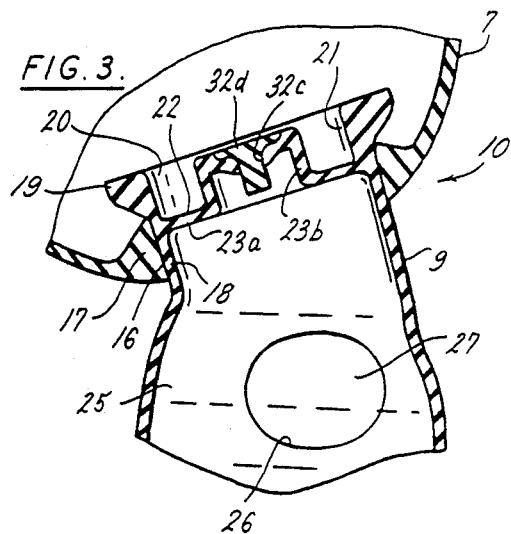
FIG. 3 is a partial cross-sectional view taken along the plane of line 3—3 in FIG. 2, showing the construction of the neck.

Referring to FIG. 3, the doll head 7 is a separate structure from the lower section, and detachable therefrom. The head is comprised of a relatively stiff but flexible material, such as a vinyl rubber compound. A variety of compositions of vinyl rubber can be used, one such composition is sold by Specialty Dispersion Company, Ray Place, Fairfield, New Jersey, U.S.A. 07006, of vinyl chloride homopolymer 9002-86-2, di iso octyl phthalate 27554-26-3, calcium carbonate 1317-65-3, and barium, calcium, zinc stabilizer (the number following each compound of the vinyl rubber material is the Chemical Abstract Services (CAS) number provided by the United States government). The head 7 has a lower circular opening defined by the inner surface 16 of the wall of an annular mount section 17. Section 17 has a triangular cross-section, as seen in FIG. 3, and is continuous and unitary with the rest of the structure of the head 7. The head 7 is designed to conform to the shape and rigidity of an infant's head.

Referring now to the separate lower doll section 8, continuous housing wall 9 forms the neck 10, the torso 11, arms 12 and legs 13. The continuous wall 9 is comprised of a flexible material, such as the vinyl rubber compound described above. The continuous wall preferably has an average thickness of 0.08 inches (0.2 cm.) with a variance of 0.04 inches 0.1 cm.). The composition and thickness of the vinyl rubber compound simulate the soft, compressible skin texture and body structure of an infant baby. The lower section housing wall 9 outlines and proportionately represents the shape of the lower body of an infant baby. The size is somewhat less than that of a baby born at nine months gestation. The proportions are preferably as follows: top of the head 7 to bottom of the feet 15—about 12½ inches (about 32 cm); and, outer portion of one of the hands 14 to the outer portion of the other hand—about 8½ inches (about 22 cm).

Referring to FIG. 3, the part of the continuous housing wall 9 which forms the neck 10 comprises a general exterior tubular section 18 which extends upwardly into an annular flanged section 19. At the top of the neck 10 is an annular recess 20 which has an annular vertical wall with inner surface 21 and an annular flat bottom surface 22 formed by annular cross web 23a. The cross web 23a extends into vertical portion 23b. The vertical portion 23b has opening 23c. The filler plug 23d fits in opening 23c and is secured therein by known means, such as glue or sonic welding, to form a watertight seal. The neck 10 simulates the weak neck of an infant baby. As a result, when one handles the doll 6, proper support must be rendered to the head 7 to support the neck 10, as would be required when handling a real infant.

Annular cap plug 24 (shown in FIG. 5) fits snugly into annular recess 20 and abuts surfaces 21 and 22. The plug 24 is a solid, rigid plastic.

The head 7 is mounted to the neck 10 by the user grasping the flanged upper neck section 19 and compressing it inward to fit within the head opening, and thence passing the flanged section 19 through the opening until the position shown in FIG. 3 is reached. The surface 16 of the head opening fits flush against the exterior of tubular section 18. The flanged section 19 acts as a detent or lug that prevents movement of the annular mount section 17 beyond it in normal use. In this position, the head 7 can be rotated to various positions about neck 10. The head 7 can be removed from neck 10 by grasping it and giving it a firm tug so that the pointed inner surface of the mount section 17 presses against the flanged lug 19 to compress it inward to allow mount section 17 to pass beyond the lug 19.

Within the lower section housing wall 9 is a reservoir 25. The reservoir 25 can hold liquid such as water. The reservoir 25 is comprised of the cavities formed inside the housing wall 9 which outlines the neck 10, torso 11, arms 12, and legs 13. All of the cavities for the neck 10, torso 11, arms 12 and legs 13 are in open and free liquid flow communication with one another. For example, FIG. 3 shows the opening 26 of the arm cavity 27 into the torso cavity 28. Thus, when the reservoir 25 is filled with liquid, the interiors of the neck 10, torso 11, arms 12, and legs 13 of the infant doll 6 are filled.

Liquid can be introduced into, and removed from, the reservoir 25 though a special assembly indicated generally as 29 in FIG. 9. The assembly 29 comprises a valve for installation in an opening in the doll body that communicates with the reservoir, and a funnel adapted to cooperate with the valve to allow liquid to be introduced into or removed from the reservoir.

In this preferred embodiment, the valve comprises a valve body 32 having first and second ends 34 and 36, respectively, and a valve passage 38 extending between the first and second ends. The valve body 32 is adapted to be installed in an opening 40 in the wall 9 of the doll body. A relatively thick-walled cylindrical sleeve 42 extends inwardly into the reservoir 25 from the opening 40. The valve body 32 fits snugly in the sleeve 42, with the first end 34 of the valve body in communication with the reservoir 25. The valve body 32 preferably has a radially projecting annular flange 44 generally adjacent the second end 36. The flange 44 preferably fits in an annular recess 46 surrounding the opening 40. The valve body 32 can be sealingly secured in the opening by adhesive, heat or sonic welding, or some other suitable means.

Figure 4:
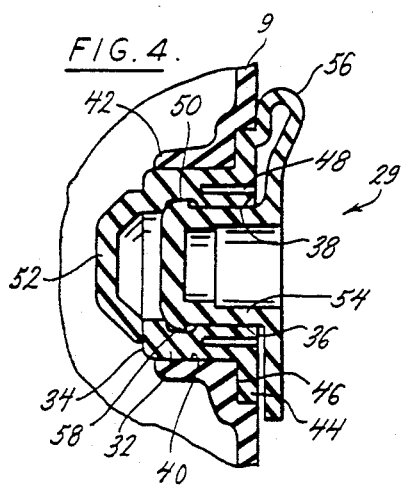
FIG. 4 is an enlarged cross-sectional view taken along the plane of line 4—4 in FIG. 2, showing the filling assembly.

As best shown in FIGS. 4 and 9, there is a generally annular cavity 48 located concentrically around the valve passage 38 and extending axially inwardly from the second end 36 of the valve body. The cavity 48 increases the flexibility of the wall of the valve passage 38 adjacent the second end 36 of the valve body. There is an annular groove 50 in the wall of the passage 38 located adjacent the "bottom" of the cavity 48.

There is a valve member at the first end 34 of the valve body, and thus when the valve body 32 is installed in the opening 40 in the doll, the valve member is located in the reservoir. The valve member is biased to close the end of the valve passage 38. In this preferred embodiment the valve member is a flap 52 hingedly attached to the first end 34 of the valve body 32. The flap 52 is circular, and generally concave. A portion of the circumference of the flap 52 is attached to the valve body 32, forming a resilient hinge. The resilience of the hinged mounting of the flap 52, the liquid pressure inside the reservoir 25, or both, bias the flap 52 to its closed position shown in FIG. 4.

A closure, for example plug 54 is preferably provided to close the passage 38 at the second end 36 of the valve body 32. The plug 54 is preferably tethered to the valve body 32 to prevent the plug from booming lost. In this preferred embodiment there is an integral flexible strap 56, extending between the flange 44 on the valve body and the plug 54. The plug 54 has a radially projecting annular ridge 58 for engaging the annular groove 50 in the wall of the passage 38, thereby retaining the plug 54 in the passage 38 until it is forcibly removed. The flexibility of the wall of the passage 38 that results from the cavity 48 facilitates the insertion and removal of the plug 54 from the passage 38.

The filling assembly also comprises funnel 60, shown in FIGS. 6 and 7. The funnel 60 has a generally converging sidewall 62 with a relatively wide opening 64 at its proximal end, and a spout 66 at its distal end. The funnel 60 has a generally bowl-shaped portion 68 adjacent the proximal end to receive and hold liquid to fill the reservoir 25. The spout 66 of the funnel 60 is adapted to seat in the valve passage 38. The end 70 of the spout 66 displaces the flap 52 (shown in FIG. 9) when the spout is properly seated in the valve passage 38 and allows liquid to pass through the valve passage. In this preferred embodiment the end 70 of the spout 66 is beveled, forming a peak 72 that displaces the flap 52, and an opening 74 in the side of the distal end of the spout for the passage of liquid into and out of the reservoir. Thus, when the spout 66 is inserted into the valve passage 38 with the bevel facing generally away form the hinge (as shown in FIG. 9), fluid can readily pass through the beveled opening of the spout. There is preferably also an opening in the peaked portion 72 of the spout 66, for example slot 76, through which fluid can pass if the funnel 60 is inserted into the valve passage with the bevel facing the hinge.

The spout 66 has a radially projecting annular ridge 78 for engaging the annular groove 50 in the wall of the passage 38, thereby retaining the spout 66 in the passage 38 until it is forcibly removed. This leaves the hands free while filling and emptying the reservoir. The flexibility of the wall of the passage 38 resulting from the cavity 48 facilitates the insertion and removal of the spout from the passage 38.

Figure 11:
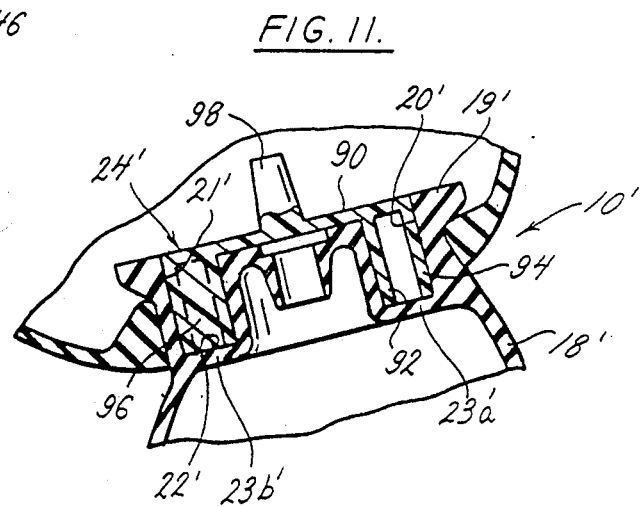
FIG. 11 is a partial cross-sectional view, similar to the view of FIG. 3, showing an alternate embodiment of the construction of the neck.

FIG. 11 shows an alternate embodiment of the neck of the doll, which is indicated generally 10'. The neck 10' is similar in construction to the neck 10 shown in FIG. 3 and described above. There is an exterior tubular section 18' that extends upwardly into an annular flanged section 19'. There is an annular recess 20' in the top of the neck. The recess 20' is defined by the inner surface 21' of the tubular section 18', a bottom surface 22' formed by annular cross web 23a', extending radially inwardly from the tubular section 18', and a cylindrical wall 23b' extending axially outwardly from the inner edge of cross web 23a'. The recess 20' of neck 10' is deeper than the recess 20 of the neck 10. Thus, as shown in FIG. 11, in neck 10' the mount section 17 of the head 7 engages the tubular section 18' generally axially above the web 23a', in contrast to the construction shown in FIG. 3, where the mount section 17 engages tubular section 18 axially below the web 23a.

Figure 12:
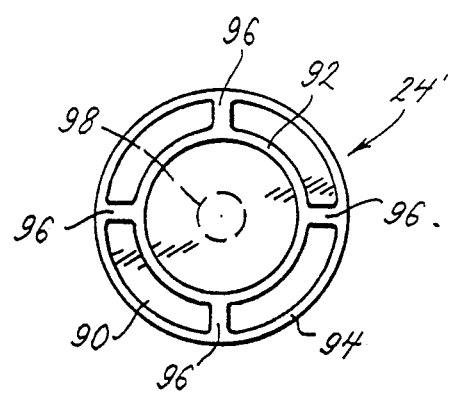
FIG. 12 is a bottom plan view of an alternate embodiment of the cap plug adapted to fit within the alternate embodiment of the neck shown in FIG. 11.

FIGS. 11 and 12 show an alternate embodiment 24' of the annular cap plug 24. The cap plug 24' fits snugly into annular recess 20' and abuts surfaces 21' and 22'. The cap plug 24' comprises circular top wall 90, a cylindrical inner wall 92 adapted to engage wall 23b', a cylindrical outer-wall 94 adapted to engage surface 21', and support ribs 96 extending radially between inner wall 92 and outer wall 94. The cap plug 24' also comprises a knob 98 extending from the center of the circular top wall 90. The oracular top wall 90, inner walls 92 and 94, ribs 96. and knob 98 preferably are formed integrally from a stiff but flexible plastic. When properly installed in the annular recess 20', the cap plug 24' closes the opening 23c. The cap plug 24' can be secured with adhesive, by some welding, or other suitable means.

Figure 10:
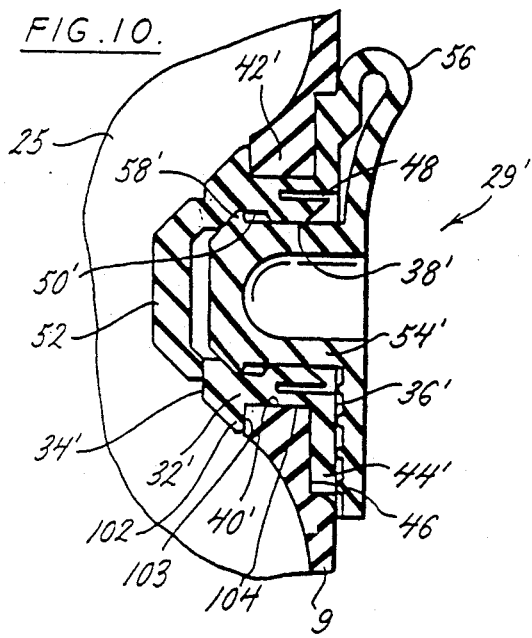
FIG. 10 is an enlarged cross-sectional view, similar to the view of FIG. 4, showing an alternative embodiment of the filling assembly.
Figure 13:
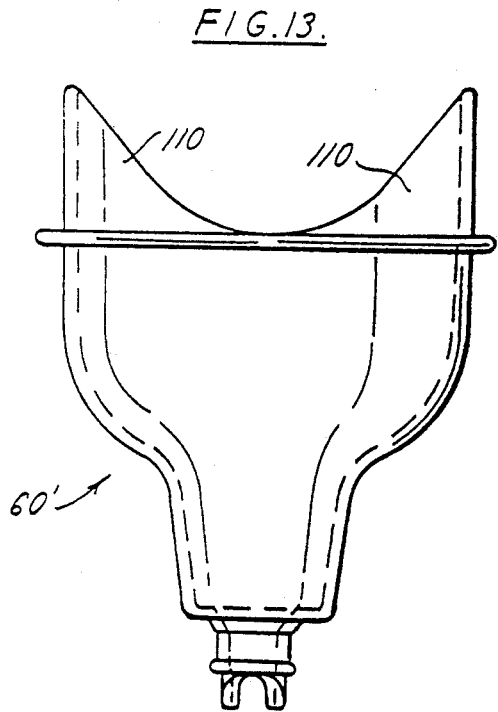
FIG. 13 is a side elevation view of an alternate embodiment of the funnel for filling and emptying the reservoir.

FIGS. 10 and 13 show an alternate preferred embodiment for the assembly 29, indicated generally as 29'. The assembly 29', like assembly 29, comprises a valve for installation in an opening in the doll body that communicates with the reservoir, and a funnel adapted to cooperate with the valve to allow liquid to be introduced into or removed from the reservoir.

In this alternate preferred embodiment, the valve comprises a valve body 32', having first and second ends 34' and 36', respectively, and a valve passage 38' extending between the first and second ends. The valve body 32' is adapted to be installed in an opening 40' in the wall 9 of the doll body. A wall surrounding the opening 40' gradually thickens toward the opening, to form a relative thick sleeve 42' around the opening 40'. The valve body 32' fits snugly within the sleeve 42', with the first end 34' of the valve body in communication with the reservoir 25. The valve body 32' has a radially projecting annular flange 44' generally adjacent the second end 36'. The flange 44' fits in an annular recess 46 in the exterior surface of the torso surrounding the opening 40'. Unlike valve body 32 of the assembly 29, valve body 32' of the assembly 29' has a radially projecting flange 102 adjacent its first end 34'. The flange 102 has a generally triangular cross-section. The flange 102 has a face 103 generally opposing the rear surface of the flange 44' to define an annular groove 104 therebetween for receiving the sleeve 42'. The face 103 of the flange 102 engages the distal end of the sleeve 42' and the back face of the flange 44' engages the proximal end of the sleeve 42', to hold the valve body 32' firmly in opening 40'. The valve body can be sealingly secured in the opening 40' by adhesive, by heat or sonic welding, or by some other suitable means.

There is a generally annular cavity 48 located concentrically around the valve passage 38' in valve body 32' and extending axially inward from the second end 36' of the valve body. As described above, with respect to valve body 32, the cavity 48 increases the flexibility of the wall of the valve passage 38' adjacent the second end 36' of the valve body. There is an annular groove 50' in the wall of the passage 38' located adjacent the "bottom" of the cavity 48.

As described above with respect to valve body 32, the valve body 32' also comprises a valve member which is configured as a flap 52. The flap 52 is hingedly attached to the first end 34' of the valve body 32' and is biased to close the valve passage 38'.

A plug 54' is provided to close the passage 38' at the second end 36' of the valve body 32'. The plug 54' is connected to the valve body 32' by an integral flexible strap 56 which extends between the flange 44 on the valve body and the plug. The plug 54' has a radially projecting annular ridge 58' for engaging the annular groove 50' in the wall of the passage 38', thereby retaining the plug 54' in the passage 38' until it is forcibly removed.

The filling assembly 29' also comprises a modified funnel 60', shown in FIG. 13. The funnel 60' is similar to the funnel 60 except that it has two rounded extensions 110 on opposite sides of the funnel 60' which give the funnel 60' a generally wavy edge. The rounded extensions help cause the funnel 60' to slide out from under the foot if the funnel is stepped upon.

OPERATION

The operation of the embodiments shown and described in FIGS. 1-9 is similar to the operation of the embodiments shown and described in FIGS. 10-13. Referring to FIG. 9, to introduce a liquid into the reservoir 25, the plug 54 must be removed to open the valve passage 38. The funnel 60 is inserted into the valve passage, until the ridge 78 is engaged in annular groove 50. Upon insertion of the funnel 60 into the valve passage 38, the end of the spout 66 displaces the flap 52. The funnel can be rotated within the passage, if desired to orient the beveled end of the spout 66 away from the hinge connecting the flap 52 to the valve body 32. Liquid can then be poured through the funnel 60 into the reservoir 25. The liquid should be poured into the funnel until the reservoir 25 is substantially filled. When the reservoir 25 is substantially filled, air bubbles or pockets may form around the filling assembly 29. While there is still liquid in the funnel 60, slight pressure can be applied to the doll back 37. This pressure will "burp" the air bubbles out of the reservoir, and allow liquid medium to fill the space previously occupied by the air bubbles or pockets. When the reservoir is filled, the funnel 60 can be removed by firmly pulling the funnel 60 outwardly out of the valve passage 38, so that ridge 78 disengages the groove 50 in the valve passage 38. As the end of the spout is pulled from the valve passage 38, the flap 52 closes the passage, either due to the resilience of the hinged mounting, the liquid pressure in the reservoir, or both. The flap 52 thus serves as a check valve, preventing the liquid from spilling out of the reservoir as the funnel is being withdrawn, and serving to reduce the liquid pressure on plug 54.

The liquid can preferably be water at 98.6° F. (37° C.) to simulate normal temperature. To simulate fever conditions, the liquid temperature can range from 99.5° F. (37.5° C.) to 106° F. (41.1° C.). The satisfaction of controlling the doll's fever can be achieved when the water with a fever temperature is used to fill the reservoir 25 can be achieved. To do this, the handler can pretend medicine is given to the doll 6, or pretend that other treatment is given, and reduce the temperature by applying ice to the housing wall 9, or by removing the hotter water from reservoir 25 and replacing it with cooler water.

As described above, the reservoir 25 is a contiguous cavity inside the housing wall 9 which defines the neck 10, the arms 12, the torso 11, and the legs 13 of the infant doll 6. When liquid is introduced into the reservoir 25, the neck 10, torso 11, arms 12, and legs 13, are filled with the liquid. When the reservoir 25 is filled, a system for transmittal of hydraulic interactive force is created among the neck 10, the torso 11, the arms 12, and the legs 13, so that when a force is exerted upon one of the body parts, the force is transmitted hydraulically to the remaining body parts. As a result, for example, if a leg 13 is grabbed or wiggled sufficiently, the remaining body parts from the neck 10 down move or wiggle. This force transmittal ability intensifies the concern that the handler will have in applying forces to the infant doll 6.

Although illustrated embodiments of the present invention have been described herein with reference to the accompanying drawings, it is to be understood that the invention is not limited to those precise embodiments, and that various other changes and modifications may be effective therein by one skilled in the art without departing from the scope or spirit of the invention.

What is claimed is:

1. In combination with a doll having a liquid fillable reservoir therein, an assembly for filling and emptying the reservoir in the doll, the assembly comprising:
   a valve incorporated into the doll, the valve comprising a valve passage communicating with the reservoir, and a valve member inside the reservoir and resiliently biased to close the end of the valve passage communicating with the reservoir; and
   a funnel having a spout adapted to seat in the valve passage, the end of the spout displacing the valve member when the spout is seated in the valve passage to allow liquid to be introduced into or removed from the reservoir through the funnel.

2. The assembly according to claim 1 wherein the valve member comprises a flap hingedly mounted over the end of the valve passage.

3. The assembly according to claim 1 wherein the end of the spout is beveled.

4. The assembly according to claim 1 further comprising an opening in the side of the spout.

5. The assembly according to claim 1 wherein the valve passage comprises cooperating means on the valve body and the funnel for releasably retaining the spout in the valve passage.

6. The assembly according to claim 5 wherein the cooperating means comprises an annular groove in the sidewall of the valve passage, and a radially projecting annular ridge on the spout adapted to engage the annular groove.

7. The assembly according to claim 6 further comprising an annular cavity surrounding a portion of the valve passage to increase the flexibility of the wall of the valve passage.

8. The assembly according to claim 1 wherein the end of the spout is adapted to project through the valve passage and into the reservoir.

9. A doll and funnel combination,
   the doll comprising at least a torso and limbs, and a permanent, flexible liquid-fillable reservoir inside the torso and limbs, the reservoir having a valve comprising a valve passage communicating with the reservoir, and a flap inside the reservoir and hingedly mounted over the valve passage to releasably close the passage;
   the funnel comprising a spout adapted to seat in, and seal with, the valve passage, the end of the spout adapted to project into the reservoir when the spout is seated in the valve passage to displace the flap and allow liquid to be introduced into or removed from the reservoir through the funnel.

10. The doll and funnel combination according to claim 9, wherein the valve comprises a separate valve body, installed in an opening in the doll that communicates with the reservoir, wherein the valve passage extends through the valve body, and wherein the flap is hingedly mounted on the valve body.

11. The doll and funnel combination according to claim 10, further comprising a plug for releasably closing the valve passage, the plug being tethered to the valve body and being adapted to fit at least partly into the valve passage.

12. The doll and funnel combination according to claim 9 further comprising cooperating means on the valve passage and on the funnel for releasably retaining the funnel spout in the valve passage.

13. The doll and funnel combination according to claim 12 wherein the cooperating means on the valve passage and the funnel comprise a raised rib on one of the valve passage or the funnel, and a groove in the other of the valve passage and the funnel for receiving and engaging the raised rib.

14. The doll and funnel combination according to claim 9 wherein the funnel has a raised rib thereon, and wherein the valve passage has a groove therein for receiving and engaging the raised rib on the funnel when the spout is seated in the valve passage.

15. The doll and funnel combination according to claim 14 further comprising an annular cavity surrounding the valve passage to increase the flexibility of the walls of the valve passage to accommodate the insertion of the funnel with the raised rib into the valve passage.

* * * * *